US00PP24756P2

(12) United States Plant Patent
Verschoor

(10) Patent No.: US PP24,756 P2
(45) Date of Patent: Aug. 12, 2014

(54) ***VERONICA* PLANT NAMED 'PINK BOMB'**

(50) Latin Name: ***Veronica* hybrid**
Varietal Denomination: Pink Bomb

(71) Applicant: Jan Verschoor, Haarlem (NL)

(72) Inventor: Jan Verschoor, Haarlem (NL)

(73) Assignee: A. Verschoor Horticulture Import—Export B.V., Haarlem (NL)

( * ) Notice: Subject to any disclaimer, the term of this patent is extended or adjusted under 35 U.S.C. 154(b) by 40 days.

(21) Appl. No.: 13/815,251

(22) Filed: Feb. 13, 2013

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Annette Para
(74) *Attorney, Agent, or Firm* — Penny J. Aguirre

(57) ABSTRACT

A new cultivar of *Veronica* plant, 'Pink Bomb', that is characterized by its flowers that are deep pink in color, its compact inflorescences with numerous flowers, and its strong, tall stems making it desirable for cut flower use.

2 Drawing Sheets

Botanical classification: *Veronica* hybrid.
Variety denomination: 'Pink Bomb'.

CROSS REFERENCE TO A RELATED APPLICATION

This application is co-pending with a U.S. Plant Patent Application filed for a plant derived from the same breeding program that is entitled *Veronica* Plant Named 'Purple Explosion' (U.S. Plant patent application Ser. No. 13/815,250).

BACKGROUND OF THE INVENTION

The present invention relates to a new and distinct cultivar of *Veronica* plant of hybrid origin and will be referred to hereinafter by its cultivar name, 'Pink Bomb'. The new cultivar of *Veronica* is a hardy herbaceous perennial grown for landscape and cut flower use.

The new cultivar of *Veronica* was discovered as a naturally occurring whole plant mutation by the Inventor in a seed bed at his nursery in July of 2010 in Haarlem, The Netherlands. The exact parentage is unknown, however the seeds were collected, pooled, and sown from open pollinated plants of 'Pink Explosion' (U.S. Plant Pat. No. 22,592), 'Blue Explosion' (U.S. Plant Pat. No. 22,497), and 'Blue Bomb' (U.S. Plant Pat. No. 22,509).

Asexual propagation of the new cultivar was first accomplished by stem cuttings by the Inventor in August of 2010 in Haarlem, The Netherlands. Asexual propagation by stem cuttings and division has shown that the characteristics of the new cultivar are stable and reproduce true to type in successive generations.

SUMMARY OF THE INVENTION

The following traits have been repeatedly observed and represent the characteristics of the new cultivar. These attributes in combination distinguish 'Pink Bomb' as a new and unique cultivar of *Veronica*.

1. 'Pink Bomb' exhibits flowers that are deep pink in color.
2. 'Pink Bomb' exhibits compact inflorescences with numerous flowers.
3. 'Pink Bomb' exhibits strong, tall (55 to 60 cm in length) stems making it desirable for cut flower use.

'Pink Bomb' can be most closely compared to its possible parent plants, 'Pink Explosion', 'Blue Explosion', and 'Blue Bomb'. 'Pink Explosion' differs from 'Pink Bomb' in having lighter pink flowers and in having shorter stems (45 to 50 cm in length). 'Blue Explosion' differs from 'Pink Bomb' in having blue flowers and in having slightly taller stems (60 to 65 cm in length). 'Blue Bomb' differs from 'Pink Bomb' in having blue flowers and in having shorter stems (35 to 40 cm in length). 'Pink Bomb' can also be compared to 'Purple Profusion'. 'Purple Profusion' differs from 'Pink Bomb' in having deep purple-pink flowers and in having taller stems (70 to 75 cm in length).

BRIEF DESCRIPTION OF THE DRAWINGS

The accompanying colored photographs illustrate the overall appearance and distinct characteristics of the new *Veronica*. The photographs were taken of a plant about two years in age as grown outdoors in a field in Haarlem, The Netherlands and placed in a pot for the photographs.

The photograph in FIG. 1 provides a side view of 'Pink Bomb' in bloom.

Figure 1:
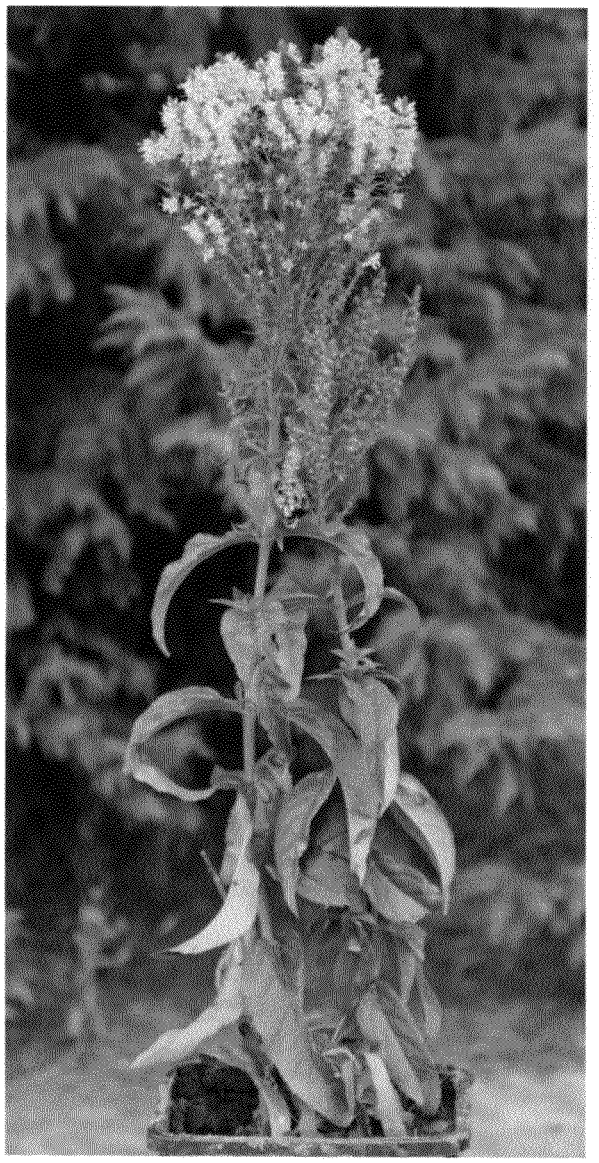
Figure 2:
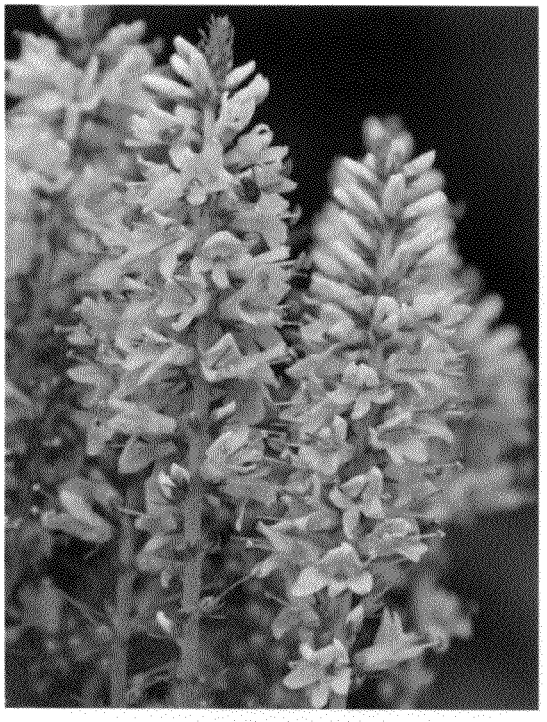

The photograph in FIG. 2 provides a close up view of the inflorescences of 'Pink Bomb'.

Figure 3:
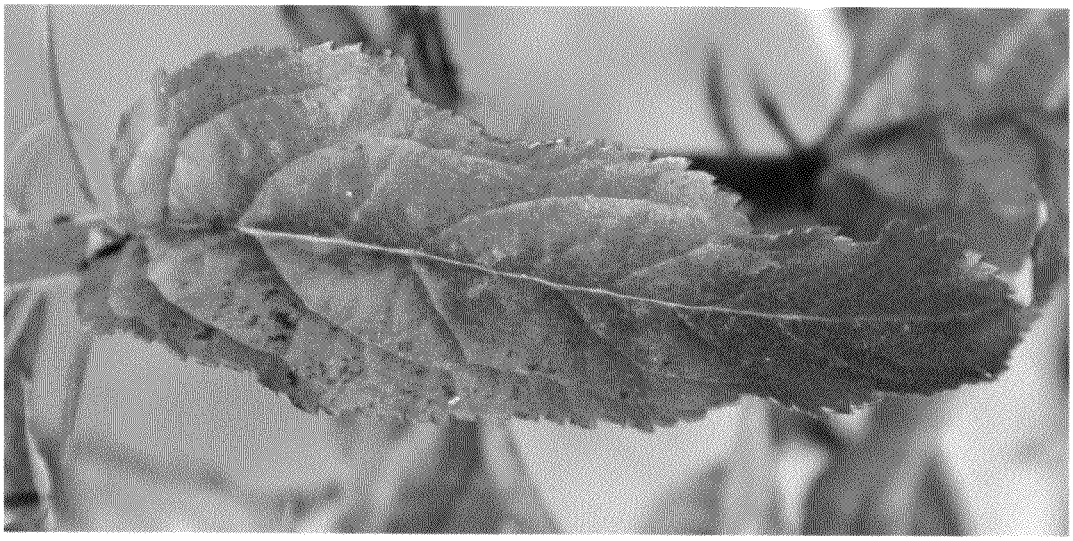

The photograph in FIG. 3 provides a close up view of a leaf of 'Pink Bomb'. The colors in the photograph may differ slightly from the color values cited in the detailed botanical description, which accurately describe the colors of the new *Veronica*.

DETAILED BOTANICAL DESCRIPTION

The following is a detailed description of the new cultivar as observed for a plant about 2-years-old as field grown outdoors in August in Haarlem, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—About 8 weeks from mid summer to early autumn in The Netherlands.

*Plant type*.—Herbaceous Perennial.

*Plant habit*.—Upright with strong, erect stems.

*Height and spread*.—Reaches about 55 cm in height (including peduncles) and about 17.5 cm in spread.

*Hardiness*.—At least hardy in U.S.D.A. Zone 4.

*Diseases*.—No particular susceptibility or resistance to diseases has been observed.

*Root description*.—Fibrous.

*Propagation*.—Division and stem cuttings.

*Growth rate*.—Moderate.

Stem description:

*Shape*.—Round.

*Stem color*.—143C.

*Stem size*.—Average of 33.8 cm in length and 5 mm in diameter.

*Stem surface*.—Slightly glossy and densely pubescent, hairs an average length of 0.5 mm and 157D in color.

*Branching number*.—Average of 2.

*Branching habit*.—Branching from the base.

Foliage description:

*Leaf division*.—Simple.

*Leaf arrangement*.—Opposite.

*Leaf shape*.—Narrowly ovate.

*Leaf size*.—An average of 9.6 cm in length and 3.2 cm length when mature.

*Leaf number*.—Average of 16 per lateral branch.

*Leaf base*.—Short attenuate.

*Leaf apex*.—Acute.

*Leaf margin*.—Serrate, average of 4.5 teeth per cm.

*Leaf venation*.—Pinnate, upper side 144A, lower side 144B.

*Leaf surface*.—Upper and lower surface moderately glossy, upper surface smooth, lower surface sparsely covered with very short hairs an average of 0.3 mm in length and to small to be measured with RHS-CC.

*Internode length*.—An average of 4.3 cm.

*Leaf color*.—Mature upper surface 147B, mature lower surface; 147B, young upper surface; 143A, young lower surface; 143B.

*Leaf attachment*.—Sessile.

*Petioles*.—V-shaped, average of 3 mm in width and 2 mm in height, 144A in color, surface pubescent.

Flower description:

*Inflorescence type*.—Compound terminal raceme.

*Lastingness of inflorescence*.—About 2 months in the garden.

*Lastingness as a cut flower*.—About 2 weeks.

*Inflorescence size*.—21.7 cm in height and 12.7 cm in width.

*Flower type*.—Campanulate.

*Flower number*.—About 1,500 per inflorescence.

*Flower fragrance*.—None.

*Flower buds*.—Ovate in shape, about 4.5 mm in length and 2.5 mm in diameter, color 68C to 68D.

*Flower size*.—About 8 mm in depth and 7 mm in diameter.

*Peduncles*.—About 21.2 cm in length and 3 mm in width, primary racemes straight upright, secondary racemes in an average angle of 40°, strong in strength, 137C in color, surface sparsely covered with very short hairs.

*Pedicels*.—An average of 1.5 mm in length and 0.5 mm in width, held at an average angle of 60°, strong in strength, 137C in color, surface sparsely covered with very short hairs.

*Calyx*.—Rotate in shape, average of 2 mm in length and 2 mm in diameter.

*Sepals*.—4, about 0.75 mm in width and 2 mm in length, young upper and lower surface color; 137B, mature upper and lower surface color; 137B to 137C, both surfaces dull and smooth, narrow ovate in shape, acute apex, cuneate base with lower 5% fused, entire margin.

*Petals*.—4, oblanceolate in shape, broadly acute apex, campanulate, lower 40% fused, entire margin, color of upper and lower surface when opening; between 65A and 68C, color of upper and lower surface when fully open; between 65A and 65C, fading to 65D, up to 5 mm in length and 2 mm in width, dull and smooth on upper and lower surface.

Reproductive organs:

*Gynoecium*.—1 Pistil, 8 mm in length, style is about 7.5 mm in length and 72B in color, stigma is clavate in shape and 156D in color, ovary is 144B in color.

*Androecium*.—2 stamens, filament is about 6 mm in length and 65D in color, anthers are dorsifixed and elliptic in shape, about 2 mm in length and N74D in color, pollen is low in quantity and 11D in color.

*Fruit*.—Fruit and seed production was not observed under the conditions tested.

It is claimed:

1. A new and distinct variety of *Veronica* plant designated 'Pink Bomb' as described and illustrated herein.

* * * * *